(12) United States Patent
Hayashi

(10) Patent No.: US 8,729,294 B2
(45) Date of Patent: May 20, 2014

(54) PROCESS FOR PRODUCING OPTICALLY ACTIVE 3-SUBSTITUTED-3-FORMYL-2-HYDROXYPROPANOIC ACID COMPOUND

(75) Inventor: Yujiro Hayashi, Miyagi (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 13/701,314

(22) PCT Filed: May 30, 2011

(86) PCT No.: PCT/JP2011/062317
§ 371 (c)(1),
(2), (4) Date: Jan. 29, 2013

(87) PCT Pub. No.: WO2011/152329
PCT Pub. Date: Dec. 8, 2011

(65) Prior Publication Data
US 2013/0137880 A1  May 30, 2013

(30) Foreign Application Priority Data
Jun. 1, 2010  (JP) .................................. 2010-125763

(51) Int. Cl.
C07C 69/675  (2006.01)
C07C 69/732  (2006.01)

(52) U.S. Cl.
USPC .......................................... 560/177; 560/212

(58) Field of Classification Search
USPC .................................................. 560/177, 212
See application file for complete search history.

(56) References Cited

U.S. PATENT DOCUMENTS 5,202,461 A  4/1993  Merger et al.
5,256,813 A  10/1993  Merger et al.

FOREIGN PATENT DOCUMENTS

| JP | 03-127759 A | 5/1991 |
| JP | 2007-182419 A | 7/2007 |
| JP | 2009-114135 A | 5/2009 |
| WO | WO 03/089396 A1 | 10/2003 |

OTHER PUBLICATIONS

Hayashi et al., *The Chemical Society of Japan Koen Yokoshu*, 91(4): 1239, Abstract C2-02 (2011).

Kano et al., *Angewandte Chemie, International Edition*, 46(10): 1738-1740 (2007).
Markert et al., *Journal of the American Chemical Society*, 131(46): 16642-16643 (2009).
Japanese Patent Office, International Search Report in International Patent Application No. PCT/JP2011/062317 (Jun. 28, 2011).

*Primary Examiner* — Shawquia Young
(74) *Attorney, Agent, or Firm* — Leydig, Voit & Mayer, Ltd.

(57) ABSTRACT

The present invention provides a production method of optically active 3-substituted-3-formyl-2-hydroxypropanoic acid compound (4), which includes a step of reacting glyoxylic acid compound (1-1) or (1-2) with aldehyde (2) in the presence of optically active pyrrolidine compound (3);

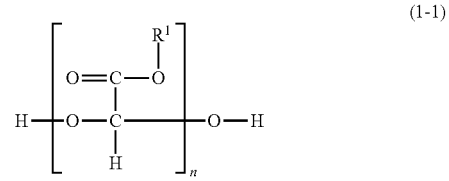

(1-1)

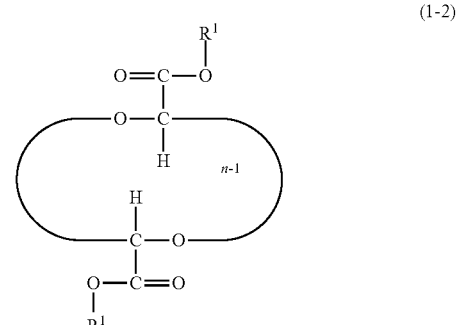

(1-2)

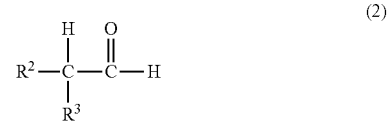

(2)

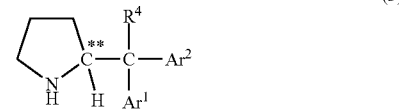

(3)

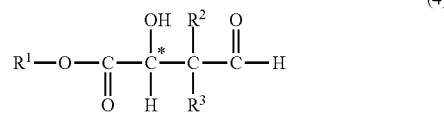

(4)

wherein each symbol is as defined in the specification.

11 Claims, No Drawings

PROCESS FOR PRODUCING OPTICALLY ACTIVE 3-SUBSTITUTED-3-FORMYL-2-HYDROXY-PROPANOIC ACID COMPOUND

CROSS-REFERENCE TO RELATED APPLICATIONS

This patent application is the U.S. national phase of International Patent Application No. PCT/JP2011/062317, filed on May 30, 2011, which claims the benefit of Japanese Patent Application No. 2010-125763, filed on Jun. 1, 2010, which are incorporated by reference in their entireties herein.

TECHNICAL FIELD

The present invention relates to a production method of an optically active 3-substituted-3-formyl-2-hydroxypropanoic acid compound.

BACKGROUND ART

An optically active 3-substituted-3-formyl-2-hydroxypropanoic acid compound is known to be useful for, for example, as a drug substance or synthetic intermediate for a medicament, a pesticide and the like, or as a synthetic intermediate for vitamins such as pantothenic acid and the like.

Concerning production method of an optically active 3-substituted-3-formyl-2-hydroxypropanoic acid compound, non-patent document 1 discloses a method of reacting ethyl glyoxylate monomer with hexanal in the presence of an axis asymmetry aminosulfonamide represented by the formula (10)

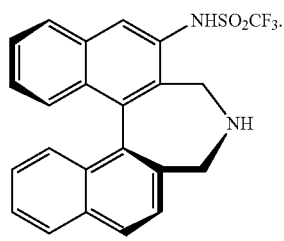

In addition, non-patent document 2 discloses a method of reacting ethyl glyoxylate polymer with isobutyraldehyde in the presence of optically active histidine.

DOCUMENT LIST

Non-Patent Document

Non-Patent Document 1: Angew. Chem. Int. Ed. 2007, 46, 1738
Non-Patent Document 2: J. Am. Chem. Soc. 2009, 131, 16642

SUMMARY OF THE INVENTION

Problems to be Solved by the Invention

An object of the present invention is to provide a new method capable of producing an optically active 3-substituted-3-formyl-2-hydroxypropanoic acid compound.

Generally, glyoxylic acid compound is commercially available in the form of a toluene solution of a polymer. Monomers are advantageous in that they have higher reactivity than polymers. While a monomer is produced by thermal decomposition of a polymer, since it has high reactivity, it easily polymerizes or immediately reacts with water. Thus, use in the form of a monomer is associated with problems of the need for thermal decomposition of the polymer, followed by distillation immediately before use, limitation to non-aqueous reactions, and the like. Therefore, use in the form of a polymer has been desired.

Means of Solving the Problems

Under the circumstances, the present inventors have studied a new production method of an optically active 3-substituted-3-formyl-2-hydroxypropanoic acid compound wherein a glyoxylic acid compound can be used in the form of a polymer, and found that a reaction in the presence of a particular asymmetric catalyst is superior in the production of an optically active 3-substituted-3-formyl-2-hydroxypropanoic acid compound, which resulted in the completion of the present invention. Accordingly, the present invention is as follows.

[1] A method of producing an optically active 3-substituted-3-formyl-2-hydroxypropanoic acid compound represented by the formula (4):

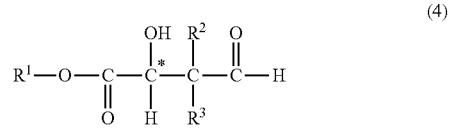

wherein
$R^1$ is a $C_1$-$C_{20}$ hydrocarbon group optionally having substituent(s) selected from the following Group G1 or a hydrogen atom,
$R^2$ and $R^3$ are each independently a $C_1$-$C_{20}$ hydrocarbon group optionally having substituent(s) selected from the following Group G1, a $C_1$-$C_{12}$ alkoxy group optionally having substituent(s) selected from the following Group G1, a heterocyclic group optionally having substituent(s) selected from the following Group G1 or a hydrogen atom, and
the carbon atom marked with * is an asymmetric carbon atom,
(hereinafter referred to as optically active 3-substituted-3-formyl-2-hydroxypropanoic acid compound (4)), which comprises a step of reacting a glyoxylic acid compound represented by the formula (1-1):

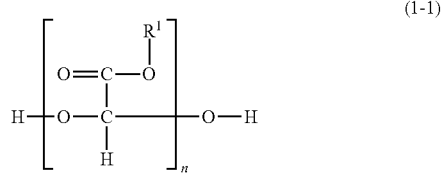

wherein $R^1$ is as defined above, and n is an integer of 2 or more (hereinafter referred to as glyoxylic acid compound (1-1)), or a glyoxylic acid compound represented by the formula (1-2):

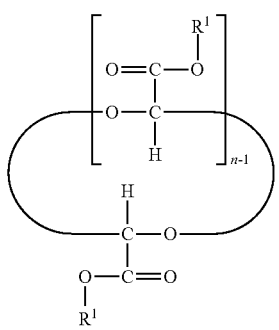

(1-2)

wherein $R^1$ and n are as defined above (hereinafter referred to as glyoxylic acid compound (1-2)) with an aldehyde represented by the formula (2):

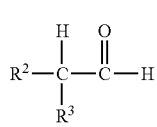

(2)

wherein $R^2$ and $R^3$ are as defined above (hereinafter referred to as aldehyde (2)) in the presence of an optically active pyrrolidine compound represented by the formula (3):

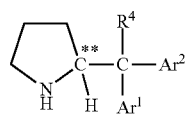

(3)

wherein
$Ar^1$ and $Ar^2$ are each independently a phenyl group optionally having substituent(s) selected from the following Group G2, a $C_1$-$C_{12}$ chain hydrocarbon group, a $C_3$-$C_{12}$ alicyclic hydrocarbon group or a hydrogen atom,
$R^4$ is a hydrogen atom, a fluorine atom, a hydroxyl group, a $C_1$-$C_{12}$ alkoxy group, a $C_1$-$C_{12}$ fluorinated alkyloxy group or a silyloxy group represented by —$OSiR^5R^6R^7$ wherein $R^5$, $R^6$ and $R^7$ are each independently a $C_1$-$C_8$ alkyl group or a $C_6$-$C_{20}$ aryl group, and
the carbon atom marked with ** is an asymmetric carbon atom, (hereinafter referred to as optically active pyrrolidine compound (3));
Group G1: the group consisting of a $C_6$-$C_{20}$ aryl group optionally having substituent(s) selected from Group G2, an aromatic heterocyclic group optionally having substituent(s) selected from Group G2, a $C_1$-$C_{12}$ alkoxy group, a $C_1$-$C_{12}$ alkoxy group having $C_6$-$C_{20}$ aryl group(s) optionally having substituent(s) selected from Group G2, a halogen atom and an oxo group;
Group G2: the group consisting of a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a $C_2$-$C_{13}$ acyl group, a nitro group, a cyano group, a protected amino group and a halogen atom.

[2] The method of the above-mentioned [1], wherein the reaction is carried out in the presence of a solvent.
[3] The method of the above-mentioned [2], wherein the solvent is at least one selected from the group consisting of an aromatic hydrocarbon solvent, an alcohol solvent, a halogenated hydrocarbon solvent, an ether solvent, a nitrile solvent and water.
[4] The method of the above-mentioned [1], wherein the reaction is carried out within the range of 0-50° C.
[5] The method of the above-mentioned [1], wherein $R^3$ is a hydrogen atom.
[6] The method of the above-mentioned [1], wherein $R^4$ is a hydroxyl group, and $Ar^1$ and $Ar^2$ are each independently a phenyl group optionally having $C_1$-$C_{12}$ fluorinated alkyl group(s).
[7] The method of the above-mentioned [1], wherein $R^4$ is a hydroxyl group, and $Ar^1$ and $Ar^2$ are both 3,5-bis(trifluoromethyl)phenyl groups.
[8] The method of the above-mentioned [6] or [7], wherein the absolute configuration of C** is S-configuration, and the absolute configuration of C* is R-configuration.
[9] A method of producing an optically active acetal compound represented by the formula (5):

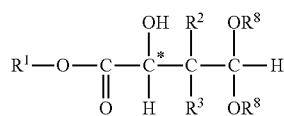

(5)

wherein
$R^1$, $R^2$ and $R^3$ are as defined in the above-mentioned [1],
$R^8$ is a $C_1$-$C_8$ alkyl group, and
the carbon atom marked with * is an asymmetric carbon atom (hereinafter referred to as optically active acetal compound (5)), which comprises a step of reacting optically active 3-substituted-3-formyl-2-hydroxypropanoic acid compound (4), which is obtained according to the method of any of the above-mentioned [1] to [8], with $R^8OH$ or $HC(OR^8)_3$ wherein $R^8$ is as defined above, in the presence of an acid catalyst.

[10] A method of producing an optically active α,β-unsaturated ester compound represented by the formula (6):

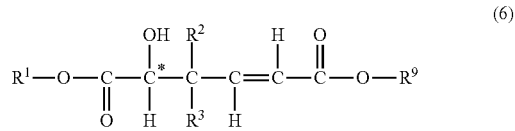

(6)

wherein
$R^1$, $R^2$ and $R^3$ are as defined in the above-mentioned [1],
$R^9$ is a $C_1$-$C_8$ alkyl group, and
the carbon atom marked with * is an asymmetric carbon atom (hereinafter referred to as optically active α,β-unsaturated ester compound (6)), which comprises a step of reacting optically active 3-substituted-3-formyl-2-hydroxypropanoic acid compound (4), which is obtained according to the method of any of the above-mentioned [1] to [8], with $Ph_3P$=$CHCO_2R^9$ wherein Ph is a phenyl group, and $R^9$ is as defined above.

Effect of the Invention

According to the production method of the present invention, since the reactivity of the reaction in the presence of optically active pyrrolidine compound (3) as a catalyst is superior even when glyoxylic acid compound (1-1) or (1-2) is used in the form of a polymer, a commercially available product can be used, and a complicated step such as thermal decomposition and distillation immediately before use is not necessary. In addition, reaction under aqueous conditions is also possible. Furthermore, when reacted in toluene, a commercially available product can be advantageously used directly without evaporating toluene.

Using optically active pyrrolidine compound (3) having a particular structure and a particular solvent, an optically active 3-substituted-3-formyl-2-hydroxypropanoic acid compound (4) can be produced in a high yield with superior enantioselectivity and diastereoselectivity (when $R^2$ and $R^3$ in aldehyde (2) are different groups).

DESCRIPTION OF EMBODIMENTS

The present invention is explained in detail below.

In the present specification, the "halogen atom" means a fluorine atom, a chlorine atom, a bromine atom or an iodine atom.

In the present specification, the "$C_1$-$C_{20}$ hydrocarbon group" means a $C_1$-$C_{20}$ aliphatic hydrocarbon group or a $C_6$-$C_{20}$ aromatic hydrocarbon group.

In the present specification, the "$C_1$-$C_{20}$) aliphatic hydrocarbon group" means a $C_1$-$C_{20}$ chain hydrocarbon group or a $C_3$-$C_{20}$ alicyclic hydrocarbon group.

In the present specification, the "$C_1$-$C_{12}$ aliphatic hydrocarbon group" means a $C_1$-$C_{12}$ chain hydrocarbon group or a $C_3$-$C_{12}$ alicyclic hydrocarbon group.

In the present specification, the "$C_1$-$C_{20}$ chain hydrocarbon group" means a $C_1$-$C_{20}$ alkyl group, a $C_2$-$C_{20}$ alkenyl group or a $C_2$-$C_{20}$ alkynyl group.

In the present specification, the "$C_1$-$C_{12}$ chain hydrocarbon group" means a $C_1$-$C_{12}$ alkyl group, a $C_2$-$C_{12}$ alkenyl group or a $C_2$-$C_{12}$ alkynyl group.

In the present specification, the "$C_1$-$C_{20}$ alkyl group" means a straight or branched chain alkyl group having 1 to 20 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, eicosyl and the like. Among them, a $C_1$-$C_{12}$ alkyl group is preferable, and a $C_1$-$C_8$ alkyl group is particularly preferable.

In the present specification, the "$C_1$-$C_{12}$ alkyl group" means a straight or branched chain alkyl group having 1 to 12 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl and the like. Among them, a $C_1$-$C_8$ alkyl group is preferable, and a $C_1$-$C_4$ alkyl group is particularly preferable.

In the present specification, the "$C_1$-$C_8$ alkyl group" means a straight or branched chain alkyl group having 1 to 8 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl and the like. Among them, a $C_1$-$C_4$ alkyl group is preferable.

In the present specification, the "$C_{1-6}$ alkyl (group)" means a straight or branched chain alkyl (group) having 1 to 6 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like. Among them, a $C_1$-$C_4$ alkyl (group) is preferable.

In the present specification, the "$C_{1-4}$ alkyl (group)" means a straight or branched chain alkyl (group) having 1 to 4 carbon atoms, and examples thereof include methyl, ethyl, propyl, isopropyl, butyl, isobutyl, sec-butyl, tert-butyl and the like.

In the present specification, the "$C_2$-$C_{20}$ alkenyl group" means a straight or branched chain alkenyl group having 2 to 20 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl, 1-nonenyl, 1-decenyl, 1-undecenyl, 1-dodecenyl, 1-tridecenyl, 1-eicosenyl and the like. Among them, a $C_2$-$C_{12}$ alkenyl group is preferable, and a $C_2$-$C_8$ alkenyl group is particularly preferable.

In the present specification, the "$C_2$-$C_{12}$ alkenyl group" means a straight or branched chain alkenyl group having 2 to 12 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl, 1-nonenyl, 1-decenyl, 1-undecenyl, 1-dodecenyl and the like. Among them, a $C_2$-$C_8$ alkenyl group is preferable, and a $C_2$-$C_4$ alkenyl group is particularly preferable.

In the present specification, the "$C_2$-$C_6$ alkenyl (group)" means a straight or branched chain alkenyl (group) having 2 to 6 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like. Among them, a $C_2$-$C_4$ alkenyl (group) is particularly preferable.

In the present specification, the "$C_2$-$C_{20}$ alkynyl group" means a straight or branched chain alkynyl group having 2 to 20 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl, 1-undecynyl, 1-dodecynyl, 1-tridecynyl, 1-eicosynyl and the like. Among them, a $C_2$-$C_{12}$ alkynyl group is preferable, and a $C_2$-$C_8$ alkynyl group is particularly preferable.

In the present specification, the "$C_2$-$C_{12}$ alkynyl group" means a straight or branched chain alkynyl group having 2 to 12 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl, 1-undecynyl, 1-dodecynyl and the like. Among them, a $C_2$-$C_8$ alkynyl group is preferable, and a $C_2$-$C_4$ alkynyl group is particularly preferable.

In the present specification, the "$C_3$-$C_{20}$ alicyclic hydrocarbon group" means a $C_3$-$C_{20}$ cycloalkyl group or a $C_4$-$C_{20}$ cycloalkenyl group.

In the present specification, the "$C_3$-$C_{12}$ alicyclic hydrocarbon group" means a $C_3$-$C_{12}$ cycloalkyl group or a $C_4$-$C_{12}$ cycloalkenyl group.

In the present specification, the "$C_3$-$C_{20}$ cycloalkyl group" means a cyclic alkyl group having 3 to 20 carbon atoms, and examples thereof include cyclopropyl, cyclobutyl, cyclopentyl, cyclohexyl, cycloheptyl, cyclooctyl, cyclononyl, cyclodecyl, cycloundecyl, cyclododecyl, cyclotridecyl, cycloeicosyl and the like. Among them, a $C_3$-$C_{12}$ cycloalkyl group is preferable, and a $C_3$-$C_8$ cycloalkyl group is particularly preferable.

In the present specification, the "$C_3$-$C_{12}$ cycloalkyl group" means a cyclic alkyl group having 3 to 12 carbon atoms, and examples thereof include cyclopropyl, cyclobutyl, cyclopentyl, cyclohexyl, cycloheptyl, cyclooctyl, cyclononyl, cyclodecyl, cycloundecyl, cyclododecyl and the like. Among them, a $C_3$-$C_8$ cycloalkyl group is preferable.

In the present specification, the "$C_4$-$C_{20}$ cycloalkenyl group" means a cyclic alkenyl group having 4 to 20 carbon atoms, and examples thereof include 2-cyclopenten-1-yl, 3-cyclopenten-1-yl, 2-cyclohexen-1-yl, 3-cyclohexen-1-yl, 2-cyclohepten-1-yl, 2-cycloocten-1-yl, 2-cyclononen-1-yl, 2-cyclodecen-1-yl, 2-cyclododecen-1-yl, 2-cycloeicosen-1-yl, 2,4-cyclopentadien-1-yl, 2,4-cyclohexadien-1-yl, 2,5-cyclohexadien-1-yl and the like. Among them, a $C_4$-$C_{12}$ cycloalkenyl group is preferable, and a $C_4$-$C_8$ cycloalkenyl group is particularly preferable.

In the present specification, the "$C_4$-$C_{12}$ cycloalkenyl group" means a cyclic alkenyl group having 4 to 12 carbon atoms, and examples thereof include 2-cyclopenten-1-yl, 3-cyclopenten-1-yl, 2-cyclohexen-1-yl, 3-cyclohexen-1-yl, 2-cyclohepten-1-yl, 2-cycloocten-1-yl, 2-cyclononen-1-yl, 2-cyclodecen-1-yl, 2-cyclododecen-1-yl, 2,4-cyclopentadien-1-yl, 2,4-cyclohexadien-1-yl, 2,5-cyclohexadien-1-yl and the like. Among them, a $C_4$-$C_8$ cycloalkenyl group is preferable.

In the present specification, the "$C_3$-$C_{20}$ cycloalkyl group", "$C_3$-$C_{12}$ cycloalkyl group", "$C_4$-$C_{20}$ cycloalkenyl group" and "$C_4$-$C_{12}$ cycloalkenyl group" are optionally fused with a benzene ring, and examples thereof include 1,2-dihydronaphthalen-1-yl, 1,2-dihydronaphthalen-2-yl, 1,2,3,4-tetrahydronaphthalen-1-yl, 1,2,3,4-tetrahydronaphthalen-2-yl, fluoren-9-yl, inden-1-yl and the like.

In the present specification, the "$C_6$-$C_{20}$ aromatic hydrocarbon group (the $C_6$-$C_{20}$ aryl group)" means a monocyclic or polycyclic (fused) hydrocarbon group having 6 to 20 carbon atoms and showing aromaticity, and examples thereof include phenyl, 1-naphthyl, 2-naphthyl, phenanthryl, anthryl, acenaphthyl, naphthacenyl, biphenylyl and the like. Among them, a $C_6$-$C_{14}$ aromatic hydrocarbon group (a $C_6$-$C_{14}$ aryl group) is preferable, and a $C_6$-$C_{10}$ aromatic hydrocarbon group (a $C_6$-$C_{10}$ aryl group) is particularly preferable.

In the present specification, the "$C_6$-$C_{12}$ aromatic hydrocarbon group (the $C_6$-$C_{12}$ aryl group)" means a monocyclic or polycyclic (fused) hydrocarbon group having 6 to 12 carbon atoms and showing aromaticity, and examples thereof include phenyl, 1-naphthyl, 2-naphthyl, acenaphthyl, biphenylyl and the like. Among them, a $C_6$-$C_{10}$ aromatic hydrocarbon group (a $C_6$-$C_{10}$ aryl group) is preferable.

In the present specification, the "$C_6$-$C_{10}$ aryl (group)" means a monocyclic or polycyclic (fused) hydrocarbon group having 6 to 10 carbon atoms and showing aromaticity, and examples thereof include phenyl, 1-naphthyl, 2-naphthyl and the like.

In the present specification, the "$C_7$-$C_{14}$ aralkyl (group)" means a "$C_{1-4}$ alkyl (group)" substituted by "$C_6$-$C_{10}$ aryl (group(s))", and examples thereof include benzyl, 1-phenylethyl, 2-phenylethyl, (1-naphthyl)methyl, (2-naphthyl)methyl, 1-(1-naphthyl)ethyl, 1-(2-naphthyl)ethyl, 2-(1-naphthyl)ethyl, 2-(2-naphthyl)ethyl and the like.

In the present specification, the "$C_1$-$C_{12}$ alkoxy group" means a straight or branched chain alkoxy group having 1 to 12 carbon atoms, and examples thereof include methoxy, ethoxy, propoxy, isopropoxy, butoxy, isobutoxy, sec-butoxy, tert-butoxy, pentyloxy, isopentyloxy, neopentyloxy, hexyloxy, heptyloxy, octyloxy, nonyloxy, decyloxy, undecyloxy, dodecyloxy and the like. Among them, a $C_1$-$C_8$ alkoxy group is preferable, and a $C_1$-$C_4$ alkoxy group is particularly preferable.

In the present specification, the "$C_1$-$C_6$ alkoxy (group)" means a straight or branched chain alkoxy (group) having 1 to 6 carbon atoms, and examples thereof include methoxy, ethoxy, propoxy, isopropoxy, butoxy, isobutoxy, sec-butoxy, tert-butoxy, pentyloxy, isopentyloxy, neopentyloxy, hexyloxy and the like. Among them, a $C_1$-$C_4$ alkoxy (group) is preferable.

In the present specification, the "heterocyclic group" means an aromatic heterocyclic group or a non-aromatic heterocyclic group.

In the present specification, the "aromatic heterocyclic group" means a monocyclic or polycyclic (fused) heterocyclic group containing, as a ring-constituting atom besides carbon atom, 1 to 4 hetero atoms selected from an oxygen atom, a sulfur atom and a nitrogen atom, and showing aromaticity.

In the present specification, examples of the "monocyclic aromatic heterocyclic group" include furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl (1,2,4-oxadiazolyl, 1,3,4-oxadiazolyl), thiadiazolyl (1,2,4-thiadiazolyl, 1,3,4-thiadiazolyl), triazolyl (1,2,4-triazolyl, 1,2,3-triazolyl), tetrazolyl, triazinyl and the like. Among them, a 5- or 6-membered monocyclic aromatic heterocyclic group is preferable.

In the present specification, the "fused aromatic heterocyclic group" means the above-mentioned monocyclic aromatic heterocyclic group fused with a monocyclic aromatic ring (preferably a benzene ring or a monocyclic aromatic heterocycle), and examples thereof include quinolyl, isoquinolyl, quinazolyl, quinoxalyl, benzofuranyl, benzothienyl, benzoxazolyl, benzisoxazolyl, benzothiazolyl, benzisothiazolyl, benzimidazolyl, benzotriazolyl, indolyl, indazolyl, pyrrolopyridyl, pyrazolopyridyl, imidazopyridyl, thienopyridyl, pyrrolopyrazinyl, pyrazolopyrazinyl, imidazopyrazinyl, thienopyrazinyl, pyrrolopyrimidinyl, pyrazolopyrimidinyl, imidazopyrimidinyl, thienopyrimidinyl, pyrazolothienyl and the like.

In the present specification, examples of the "monocyclic aromatic heterocycle" include furan, thiophene, pyridine, pyrimidine, pyridazine, pyrazine, pyrrole, imidazole, pyrazole, thiazole, isothiazole, oxazole, isoxazole, oxadiazole (1,2,4-oxadiazole, 1,3,4-oxadiazole), thiadiazole (1,2,4-thiadiazole, 1,3,4-thiadiazole), triazole (1,2,4-triazole, 1,2,3-triazole), tetrazole, triazine and the like. Among them, a 5- or 6-membered monocyclic aromatic heterocycle is preferable.

In the present specification, the "non-aromatic heterocyclic group" means a monocyclic or fused heterocyclic group containing, as a ring-constituting atom besides carbon atom, 1 to 4 hetero atoms selected from an oxygen atom, a sulfur atom and a nitrogen atom, and not showing aromaticity.

Examples of the "monocyclic non-aromatic heterocyclic group" include aziridinyl, azetidinyl, pyrrolidinyl, piperidyl, azepanyl, piperazinyl, morpholinyl, thiomorpholinyl, oxazolidinyl, thiazolidinyl, imidazolidinyl, oxazolinyl, imidazolinyl, pyrazolidinyl, dioxolyl, dioxolanyl, dihydrooxadiazolyl, pyranyl, dihydropyranyl, tetrahydropyranyl, thiopyranyl, dihydrothiopyranyl, tetrahydrothiopyranyl, tetrahydrofuryl, dihydropyridyl, tetrahydropyridyl, tetrahydropyrimidinyl and the like.

In the present specification, the "fused non-aromatic heterocyclic group" means the above-mentioned monocyclic non-aromatic heterocyclic group fused with a monocyclic aromatic ring (preferably a benzene ring or a monocyclic aromatic heterocycle), or a fully or partially-saturated group thereof, and examples thereof include dihydroindolyl, dihydroisoindolyl, dihydrobenzofuranyl, tetrahydrobenzofuranyl, dihydrobenzodioxinyl, dihydrobenzodioxepinyl, chromenyl, dihydrochromenyl, dihydroquinolinyl, tetrahydroquinolinyl, dihydroisoquinolinyl, tetrahydroisoquinolinyl, dihydrophthalazinyl, azabicyclohexyl and the like.

In the present specification, the "$C_1$-$C_{12}$ fluorinated alkyl (group)" means a "$C_{1-12}$ alkyl (group)" substituted by fluorine atom(s). The number of the fluorine atoms is not particularly limited, and the $C_1$-$C_{12}$ fluorinated alkyl (group) may be perfluoro-substituted. Specific examples thereof include fluoromethyl, difluoromethyl, trifluoromethyl, 2-fluoroethyl, 2,2-difluoroethyl, 2,2,2-trifluoroethyl, 3-fluoropropyl, 4-fluorobutyl, 5-fluoropentyl, 6-fluorohexyl, 7-fluoroheptyl, 8-fluorooctyl, 9-fluorononyl, 10-fluorodecyl, 11-fluoroundecyl, 12-fluorododecyl and the like.

In the present specification, the "$C_1$-$C_{12}$ fluorinated alkyloxy group" means a "$C_{1-12}$ alkoxy group" substituted by fluorine atom(s). The number of the fluorine atoms is not particularly limited, and the $C_1$-$C_{12}$ fluorinated alkyloxy group may be perfluoro-substituted. Specific examples thereof include fluoromethoxy, difluoromethoxy, trifluoromethoxy, 2-fluoroethoxy, 2,2-difluoroethoxy, 2,2,2-trifluoroethoxy, 3-fluoropropoxy, 4-fluorobutoxy, 5-fluoropentyloxy, 6-fluorohexyloxy, 7-fluoroheptyloxy, 8-fluorooctyloxy, 9-fluorononyloxy, 10-fluorodecyloxy, 11-fluoroundecyloxy, 12-fluorododecyloxy and the like.

In the present specification, the "$C_2$-$C_{13}$ alkoxycarbonyl group" means a group wherein a "$C_1$-$C_{12}$ alkoxy group" is bonded to —C=O—, and examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl and the like. Among them, a $C_2$-$C_9$ alkoxycarbonyl group is preferable, and a $C_2$-$C_5$ alkoxycarbonyl group is particularly preferable.

In the present specification, the "$C_2$-$C_{13}$ acyl group" is a residue obtained by removing a hydroxyl group from a $C_2$-$C_{13}$ carboxylic acid, and it means a "$C_2$-$C_{13}$ aliphatic acyl group" or a "$C_7$-$C_{13}$ aromatic acyl group".

In the present specification, the "$C_2$-$C_{13}$ aliphatic acyl group" means a group wherein a "$C_1$-$C_{12}$ aliphatic hydrocarbon group" is bonded to —C=O—, and examples thereof include acetyl, propanoyl, butanoyl, 2-methylpropanoyl, pentanoyl, hexanoyl, heptanoyl, octanoyl, nonanoyl, decanoyl, undecanoyl, dodecanoyl, acryloyl, methacryloyl, crotonoyl, isocrotonoyl, propionoyl, cyclopentylcarbonyl, cyclohexylcarbonyl and the like. Among them, a $C_2$-$C_{13}$ alkylcarbonyl group is preferable, and a $C_2$-$C_9$ alkylcarbonyl group is particularly preferable.

In the present specification, the "$C_7$-$C_{13}$ aromatic acyl group" means a group wherein a "$C_6$-$C_{12}$ aromatic hydrocarbon group (a $C_6$-$C_{12}$ aryl group)" is bonded to —C=O—, and examples thereof include benzoyl, 1-naphthoyl, 2-naphthoyl and the like.

In the present specification, the "protected amino group" means an amino group protected by a "protecting group". Examples of the "protecting group" include a $C_{1-6}$ alkyl group, a $C_{2-6}$ alkenyl group, a $C_{6-10}$ aryl group, a $C_{7-14}$ aralkyl group, a $C_{1-6}$ alkyl-carbonyl group, a $C_{1-6}$ alkoxy-carbonyl group, a $C_{2-6}$ alkenyl-oxycarbonyl group, a $C_{6-10}$ aryl-carbonyl group, a $C_{7-14}$ aralkyl-carbonyl group, a $C_{6-10}$ aryl-oxycarbonyl group, a $C_{7-14}$ aralkyl-oxycarbonyl group, a $C_{6-10}$ arylsulfonyl group, a benzhydryl group, a trityl group, a tri-$C_{1-6}$ alkylsilyl group, a 9-fluorenylmethyloxycarbonyl group, a phthaloyl group and the like. The above-mentioned protecting group is optionally substituted by a halogen atom, a $C_{1-6}$ alkyl group, a $C_{1-6}$ alkoxy group or a nitro group.

Specific examples of the protecting group include acetyl, trifluoroacetyl, pivaloyl, tert-butoxycarbonyl, 2,2,2-trichloroethoxycarbonyl, benzyloxycarbonyl, 9-fluorenylmethyloxycarbonyl, benzhydryl, trityl, phthaloyl, allyloxycarbonyl, p-toluenesulfonyl, o-nitrobenzenesulfonyl and the like.

Each group of the formulas (1-1), (1-2) and (2)-(6) is explained below.

$R^1$ is a $C_1$-$C_{20}$ hydrocarbon group optionally having substituent(s) selected from Group G1 or a hydrogen atom. The number of the substituents for the $C_1$-$C_{20}$ hydrocarbon group is preferably 1 to 3. When it is 2 or more, these substituents may be the same or different.

$R^1$ is preferably a $C_1$-$C_{20}$ hydrocarbon group optionally having substituent(s) selected from Group G1, more preferably a $C_1$-$C_{20}$ alkyl group optionally having substituent(s) selected from Group G1, further more preferably a $C_1$-$C_{12}$ alkyl group optionally having substituent(s) selected from Group G1, still more preferably a $C_1$-$C_8$ alkyl group optionally having substituent(s) selected from Group G1, particularly preferably a $C_1$-$C_4$ alkyl group (particularly ethyl group).

n is an integer of 2 or more.

n is preferably an integer of 3 to 100000.

$R^2$ and $R^3$ are each independently a $C_1$-$C_{20}$ hydrocarbon group optionally having substituent(s) selected from Group G1, a $C_1$-$C_{12}$ alkoxy group optionally having substituent(s) selected from Group G1, a heterocyclic group optionally having substituent(s) selected from Group G1 or a hydrogen atom. The number of the substituents for the $C_1$-$C_{20}$ hydrocarbon group, $C_1$-$C_{12}$ alkoxy group and heterocyclic group is preferably 1 to 3. When it is 2 or more, these substituents may be the same or different.

$R^2$ is preferably a $C_1$-$C_{20}$ alkyl group optionally having substituent(s) selected from Group G1, a $C_1$-$C_{12}$ alkoxy group optionally having substituent(s) selected from Group G1, a heterocyclic group optionally having substituent(s) selected from Group G1 or a hydrogen atom, more preferably a $C_1$-$C_{12}$ alkyl group optionally having substituent(s) selected from Group G1, a $C_1$-$C_8$ alkoxy group optionally having substituent(s) selected from Group G1, a non-aromatic heterocyclic group optionally having substituent(s) selected from Group G1 or a hydrogen atom, further more preferably a $C_1$-$C_8$ alkyl group optionally having substituent(s) selected from Group G1, a $C_1$-$C_4$ alkoxy group optionally having substituent(s) selected from Group G1, a non-aromatic heterocyclic group optionally having substituent(s) selected from Group G1 or a hydrogen atom, still more preferably a $C_1$-$C_4$ alkyl group optionally having substituent(s) selected from Group G1, a $C_1$-$C_4$ alkoxy group optionally having substituent(s) selected from Group G1, a non-aromatic heterocyclic group optionally having substituent(s) selected from Group G1 or a hydrogen atom, particularly preferably (1) a hydrogen atom, (2) a $C_1$-$C_4$ alkyl group optionally having substituent(s) selected from (i) a $C_6$-$C_{20}$ aryl group (preferably a $C_6$-$C_{10}$ aryl group, particularly preferably a phenyl group), and (ii) a $C_1$-$C_{12}$ alkoxy group (preferably a $C_1$-$C_8$ alkoxy group, particularly preferably a $C_1$-$C_4$ alkoxy group) having $C_6$-$C_{20}$ aryl group(s) (preferably $C_6$-$C_{10}$ aryl group(s), particularly preferably phenyl group(s)) optionally having $C_1$-$C_{12}$ alkoxy group(s) (preferably $C_1$-$C_8$ alkoxy group(s), particularly preferably $C_1$-$C_4$ alkoxy group(s)), (3) a $C_1$-$C_4$ alkoxy group optionally having $C_6$-$C_{20}$ aryl group(s) (preferably $C_6$-$C_{10}$ aryl group(s), particularly preferably phenyl), or (4) an N-containing non-aromatic heterocyclic group (preferably isoindolyl) optionally having oxo group(s).

Specific preferable examples of $R^2$ include a hydrogen atom, methyl, ethyl, propyl, isopropyl, benzyl, benzyloxy, p-methoxybenzyloxymethyl, 1,3-dioxoisoindolyl and the like.

$R^3$ is preferably a hydrogen atom.

$Ar^1$ and $Ar^2$ are each independently a phenyl group optionally having substituent(s) selected from Group G2, a $C_1$-$C_{12}$ chain hydrocarbon group, a $C_3$-$C_{32}$ alicyclic hydrocarbon group or a hydrogen atom. The number of the substituents for the phenyl group is preferably 1 to 3. When it is 2 or more, these substituents may be the same or different.

$Ar^1$ and $Ar^2$ are preferably each independently a phenyl group optionally having substituent(s) selected from Group G2, more preferably each independently a phenyl group optionally having $C_1$-$C_{12}$ fluorinated alkyl group(s), further more preferably each independently a phenyl group optionally having $C_1$-$C_4$ fluorinated alkyl group(s), still more preferably each independently a phenyl group optionally having trifluoromethyl group(s), still more preferably both phenyl groups or both 3,5-bis(trifluoromethyl)phenyl groups, particularly preferably both 3,5-bis(trifluoromethyl)phenyl groups.

$R^4$ is a hydrogen atom, a fluorine atom, a hydroxyl group, a $C_1$-$C_{12}$ alkoxy group, a $C_1$-$C_{12}$ fluorinated alkyloxy group or a silyloxy group represented by —$OSiR^5R^6R^7$ wherein $R^5$, $R^6$ and $R^7$ are each independently a $C_1$-$C_8$ alkyl group or a $C_6$-$C_{20}$ aryl group.

$R^4$ is preferably a hydroxyl group or a silyloxy group represented by —$OSiR^5R^6R^7$ wherein $R^5$, $R^6$ and $R^7$ are as defined above, more preferably a hydroxyl group, or a silyloxy group represented by —$OSiR^5R^6R^7$ wherein $R^5$, $R^6$ and $R^7$ are each independently a $C_1$-$C_8$ alkyl group (preferably a methyl group), particularly preferably a hydroxyl group.

Preferable combination of $Ar^1$, $Ar^2$ and $R^4$ is as follows:

(1) An embodiment wherein $Ar^1$ and $Ar^2$ are each independently a phenyl group optionally having substituent(s) selected from Group G2, and $R^4$ is a hydroxyl group.

(2) An embodiment wherein $Ar^1$ and $Ar^2$ are each independently a phenyl group optionally having $C_1$-$C_{12}$ fluorinated alkyl group(s), and $R^4$ is a hydroxyl group.

(3) An embodiment wherein $Ar^1$ and $Ar^2$ are each independently a phenyl group optionally having $C_1$-$C_4$ fluorinated alkyl group(s), and $R^4$ is a hydroxyl group.

(4) An embodiment wherein $Ar^1$ and $Ar^2$ are each independently a phenyl group optionally having trifluoromethyl group(s), and $R^4$ is a hydroxyl group.

(5) An embodiment wherein $Ar^1$ and $Ar^2$ are both phenyl groups or both 3,5-bis(trifluoromethyl)phenyl groups, and $R^4$ is a hydroxyl group.

(6) An embodiment wherein $Ar^1$ and $Ar^2$ are both 3,5-bis(trifluoromethyl)phenyl groups, and $R^4$ is a hydroxyl group.

$R^8$ is a $C_1$-$C_8$ alkyl group.

$R^8$ is preferably a $C_1$-$C_4$ alkyl group (particularly methyl).

$R^9$ is a $C_1$-$C_8$ alkyl group.

$R^9$ is preferably a $C_1$-$C_4$ alkyl group (particularly ethyl, tert-butyl).

In the present invention, optically active 3-substituted-3-formyl-2-hydroxypropanoic acid compound (4) is produced by a step of reacting glyoxylic acid compound (1-1) or (1-2) with aldehyde (2) in the presence of optically active pyrrolidine compound (3) as a catalyst (aldol reaction step).

Glyoxylic acid compound (1-1) or (1-2) is a polymer of the glyoxylic acid compound represented by the formula (1'):

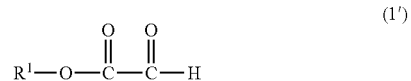

wherein $R^1$ are as defined above. Generally, glyoxylic acid compound is commercially available in the form of a toluene solution of a polymer (i.e., glyoxylic acid compound (1-1) or (1-2)). Monomers are advantageous in that they have higher reactivity than polymers. While a monomer (i.e., glyoxylic acid compound (1')) is produced by thermal decomposition of a polymer, since it has high reactivity, it easily polymerizes or immediately reacts with water. Thus, use in the form of a monomer is associated with problems of the need for thermal decomposition of the polymer, followed by distillation immediately before use, limitation to non-aqueous reactions, and the like.

The reactivity is superior in the aldol reaction step in the present invention even by use in the form of a polymer. Therefore, a commercially available product can be used, and a complicated step such as thermal decomposition and distillation immediately before use is not necessary. In addition, reaction under aqueous conditions is also possible. Furthermore, when reacted in toluene, a commercially available product can be advantageously used directly without evaporating toluene.

The amount of aldehyde (2) to be used is preferably 0.5-10 mol, more preferably 0.5-5 mol, per 1 mol of glyoxylic acid compound (1-1) or (1-2) (in monomer amount), in view of yield, selectivity and economic efficiency.

The catalyst, optically active pyrrolidine compound (3) is preferably an optically active pyrrolidine compound represented by the formula (3a):

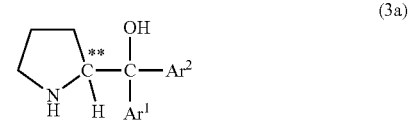

wherein $Ar^1$ and $Ar^2$ are as defined above, and the carbon atom marked with ** is an asymmetric carbon atom, in view of diastereoselectivity (when $R^2$ and $R^3$ of aldehyde (2) are different groups), though depending on the kind of aldehyde (2). Among them, an optically active pyrrolidine compound wherein $Ar^1$ and $Ar^2$ are each independently a phenyl group optionally having $C_1$-$C_4$ fluorinated alkyl group(s) is preferable, an optically active pyrrolidine compound wherein $Ar^1$ and $Ar^2$ are each independently a phenyl group optionally having trifluoromethyl group(s) is more preferable, an optically active pyrrolidine compound wherein $Ar^1$ and $Ar^2$ are both phenyl groups or both 3,5-bis(trifluoromethyl)phenyl groups is still more preferable, and an optically active pyrrolidine compound wherein $Ar^1$ and $Ar^2$ are both 3,5-bis(trifluoromethyl)phenyl groups is particularly preferable.

The amount of optically active pyrrolidine compound (3) to be used is preferably 0.5-30 mol %, more preferably 1-20 mol %, particularly preferably 5-15 mol %, relative to glyoxylic acid compound (1-1) or (1-2) (in monomer amount), in view of yield and economic efficiency.

The aldol reaction step of the present invention is preferably carried out in the presence of a solvent. Examples of the solvent to be used in the present invention include an aromatic hydrocarbon solvent (e.g., toluene, benzene, xylene); an alcohol solvent (e.g., methanol, ethanol); a halogenated hydrocarbon solvent (e.g., chloroform, dichloromethane, carbon tetrachloride); an ether solvent (e.g., diethyl ether, tetrahydrofuran); a nitrile solvent (e.g., acetonitrile); an aprotic polar solvent (e.g., dimethylformamide, dimethylacetamide); water; a mixed solvent thereof and the like.

An aromatic hydrocarbon solvent; an alcohol solvent; a halogenated hydrocarbon solvent; an ether solvent; a nitrile solvent; water; a mixed solvent thereof and the like are preferable from among them in view of enantioselectivity and diastereoselectivity (when $R^2$ and $R^3$ of aldehyde (2) are different groups), and a mixed solvent of nitrile solvent and water is particularly preferable in view of superior enantioselectivity and diastereoselectivity, though depending on the kind of aldehyde (2). When the solvent is a mixed solvent of nitrile solvent and water, the amount of water to be used is preferably 1-5 mol, more preferably 2-4 mol, per 1 mol of the nitrile solvent.

The amount of the solvent to be used is preferably 0.2-20 mL per 1 g of aldehyde compound (2).

When the aldol reaction is carried out in a solvent free of toluene, glyoxylic acid compound (1-1) or (1-2) after concentrating the commercially available toluene solution is used.

The aldol reaction step of the present invention is carried out by a method of adding aldehyde (2), optically active pyrrolidine compound (3) and solvent to glyoxylic acid compound (1-1) or (1-2), and then mixing them; a method of mixing glyoxylic acid compound (1-1) or (1-2), optically active pyrrolidine compound (3) and solvent, and then adding aldehyde (2) thereto; and the like. In view of yield and selectivity, the step is preferably carried out by a method of adding aldehyde (2), optically active pyrrolidine compound (3) and solvent to glyoxylic acid compound (1-1) or (1-2), and then mixing them.

The aldol reaction step in the present invention is carried out preferably within the range of 0-50° C., more preferably within the range of 0-40° C., though depending on the kind of aldehyde (2).

While the reaction time varies depending on the kind of aldehyde (2) and the reaction temperature, it is preferably 1-100 hr, more preferably 10-50 hr, particularly preferably 20-40 hr.

The progress of the reaction can be confirmed by an analysis means such as thin layer chromatography, gas chromatography, high performance liquid chromatography and the like.

Optically active 3-substituted-3-formyl-2-hydroxypropanoic acid compound (4) contained in thus obtained reaction mixture can be isolated by subjecting the reaction mixture to a post-treatment using a conventional method (e.g., neutralization, extraction, washing with water, distillation, crystallization etc.), and purified by subjecting optically active 3-substituted-3-formyl-2-hydroxypropanoic acid compound (4) to recrystallization treatment, extraction purification treatment, distillation treatment, adsorption treatment using activated carbon, silica, alumina and the like, or chromatography treatment using silica gel column chromatography and the like.

When $R^2$ and $R^3$ in aldehyde (2) are different groups, diastereomers (syn-form and anti-form) exist. Optically active 3-substituted-3-formyl-2-hydroxypropanoic acid compound (4) may be isomerized during isolation and/or purification from the reaction mixture. Therefore, the diastereo ratio (syn/anti ratio) and enantiomeric excess (ee(%)) of optically active 3-substituted-3-formyl-2-hydroxypropanoic acid compound (4) are desirably measured without isolation and/or purification after completion of the aldol reaction, but after conversion of 3-substituted-3-formyl-2-hydroxypropanoic acid compound (4) to a compound free of isomerization during reaction, isolation and purification. In the present invention, optically active 3-substituted-3-formyl-2-hydroxypropanoic acid compound (4) is converted to a corresponding acetal compound (an optically active acetal compound represented by the formula (5):

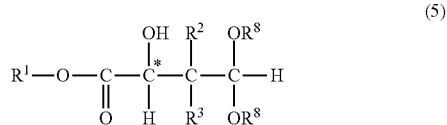

(5)

wherein $R^1$, $R^2$, $R^3$ and $R^8$ are as defined above, and the carbon atom marked with * is an asymmetric carbon atom), or a corresponding optically active α,β-unsaturated ester compound (an optically active α,β-unsaturated ester compound represented by the formula (6):

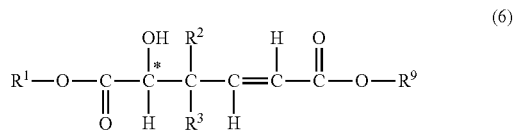

(6)

wherein $R^2$, $R^3$ and $R^9$ are as defined above, and the carbon atom marked with * is an asymmetric carbon atom).

Optically active acetal compound (5) is produced by a step of reacting the reaction mixture after completion of the aldol reaction which contains optically active 3-substituted-3-formyl-2-hydroxypropanoic acid compound (4), or optically active 3-substituted-3-formyl-2-hydroxypropanoic acid compound (4) after isolation but without purification, with $R^8OH$ or $HC(OR^8)_3$ wherein $R^8$ is as defined above, in the presence of an acid catalyst (acetalization reaction step).

Optically active acetal compound (5) is preferably produced by, (A) a step of reacting optically active 3-substituted-3-formyl-2-hydroxypropanoic acid compound (4) after isolation but without purification with $R^8OH$ wherein $R^8$ is as defined above in the presence of an acid catalyst, or (B) a step of reacting the reaction mixture after completion of the aldol reaction which contains optically active 3-substituted-3-formyl-2-hydroxypropanoic acid compound (4) with $HC(OR^8)_3$ wherein $R^8$ is as defined above in the presence of an acid catalyst.

First, step A is explained below.

The amount of $R^8OH$ to be used is preferably 2-200 mol, more preferably 10-100 mol, per 1 mol of optically active 3-substituted-3-formyl-2-hydroxypropanoic acid compound (4), in view of yield and economic efficiency. In step A, $R^8OH$ can also be a reaction solvent.

Examples of the acid catalyst to be used include pyridinium p-toluenesulfonate, and p-toluenesulfonic acid and a hydrate (monohydrate) thereof. Among them, pyridinium p-toluenesulfonate is preferable in view of reaction selectivity.

The amount of the acid catalyst to be used is preferably 0.01-1 mol, more preferably 0.01-0.1 mol, per 1 mol of optically active 3-substituted-3-formyl-2-hydroxypropanoic acid compound (4), in view of reactive and economic efficiency.

The acetalization reaction is carried out by a method of adding $R^8OH$ and an acid catalyst to optically active 3-substituted-3-formyl-2-hydroxypropanoic acid compound (4) after isolation but without purification, and the mixing them; a method of adding an acid catalyst to optically active 3-substituted-3-formyl-2-hydroxypropanoic acid compound (4) after isolation but without purification, and then adding $R^8OH$ thereto, and mixing them; and the like. In view of convenient operation, a method of adding $R^8OH$ and an acid catalyst to optically active 3-substituted-3-formyl-2-hydroxypropanoic acid compound (4) after isolation but without purification, and mixing them is preferable.

The acetalization reaction is carried out preferably within the range of 0-100° C., more preferably within the range of 20-80° C., particularly preferably within the range of 40-60° C., though depending on the kind of $R^8OH$ and the acid catalyst.

While the reaction time varies depending on the kind of $R^8OH$ and the acid catalyst, and the reaction temperature, it is preferably 10 min-50 hr, more preferably 30 min-20 hr, particularly preferably 1-10 hr.

The progress of the reaction can be confirmed by an analysis means such as thin layer chromatography, gas chromatography, high performance liquid chromatography and the like.

Next, step B is explained below.

The amount of $HC(OR^8)_3$ to be used is preferably 1-20 mol, more preferably 3-10 mol, per 1 mol of optically active 3-substituted-3-formyl-2-hydroxypropanoic acid compound (4), in view of yield and economic efficiency.

Examples of the acid catalyst to be used include p-toluenesulfonic acid and a hydrate (monohydrate) thereof, and pyridinium p-toluenesulfonate. Among them, p-toluenesulfonic acid and a hydrate (monohydrate) thereof are preferable in view of yield and economic efficiency.

The amount of the acid catalyst to be used is preferably 0.01-1 mol, more preferably 0.01-0.1 mol, per 1 mol of optically active 3-substituted-3-formyl-2-hydroxypropanoic acid compound (4), in view of reaction rate.

The acetalization reaction is carried out by a method of adding $HC(OR^8)_3$ and an acid catalyst to the reaction mixture after completion of the aldol reaction which contains optically active 3-substituted-3-formyl-2-hydroxypropanoic acid compound (4), and mixing them; a method of adding an acid catalyst to the reaction mixture after completion of the aldol reaction which contains optically active 3-substituted-3-formyl-2-hydroxypropanoic acid compound (4), and then adding $HC(OR^8)_3$, and mixing them; and the like. Among them, a method of adding $HC(OR^8)_3$ and an acid catalyst to the reaction mixture after completion of the aldol reaction which contains optically active 3-substituted-3-formyl-2-hydroxypropanoic acid compound (4), and mixing them is preferable in view of convenient operation.

The acetalization reaction is carried out preferably within the range of 0-100° C., more preferably within the range of 10-40° C., particularly preferably within the range of 20-30° C., though depending on the kind of $HC(OR^8)_3$ and the acid catalyst.

While the reaction time varies depending on the kind of $HC(OR^8)_3$ and the acid catalyst, and the reaction temperature, it is preferably 10 min-50 hr, more preferably 30 min-20 hr, particularly preferably 1-10 hr.

The progress of the reaction can be confirmed by an analysis means such as thin layer chromatography, gas chromatography, high performance liquid chromatography and the like.

Optically active acetal compound (5) contained in thus obtained reaction mixture can be isolated by subjecting the reaction mixture to a post-treatment using a conventional method (e.g., neutralization, extraction, washing with water, distillation, crystallization etc.), and purified by subjecting optically active acetal compound (5) to recrystallization treatment, extraction purification treatment, distillation treatment, adsorption treatment using activated carbon, silica, alumina and the like, or chromatography treatment using silica gel column chromatography and the like.

Optically active α,β-unsaturated ester compound (6) is produced by a step of reacting the reaction mixture after completion of the aldol reaction which contains optically active 3-substituted-3-formyl-2-hydroxypropanoic acid compound (4), or optically active 3-substituted-3-formyl-2-hydroxypropanoic acid compound (4) after isolation but without purification, with $Ph_3P=CHCO_2R^9$ wherein Ph and $R^9$ are as defined above (Wittig reaction step).

The amount of $Ph_3P=CHCO_2R^9$ to be used is preferably 0.01-5 mol, more preferably 0.5-2 mol, per 1 mol of optically active 3-substituted-3-formyl-2-hydroxypropanoic acid compound (4), in view of yield and economic efficiency.

When optically active 3-substituted-3-formyl-2-hydroxypropanoic acid compound (4) after isolation but without purification is used, examples of the solvent to be used for the Wittig reaction include an aromatic hydrocarbon solvent (e.g., toluene, benzene, xylene); an alcohol solvent (e.g., methanol, ethanol); a halogenated hydrocarbon solvent (e.g., chloroform, dichloromethane, carbon tetrachloride); an ether solvent (e.g., diethyl ether, tetrahydrofuran); a nitrile solvent (e.g., acetonitrile); an aprotic polar solvent (e.g., dimethylformamide, dimethylacetamide); a mixed solvent thereof and the like. The amount of the solvent to be used is preferably 5-100 mL per 1 g of optically active 3-substituted-3-formyl-2-hydroxypropanoic acid compound (4).

The Wittig reaction is carried out by a method of adding $Ph_3P=CHCO_2R^9$ to the reaction mixture after completion of the aldol reaction which contains optically active 3-substituted-3-formyl-2-hydroxypropanoic acid compound (4), or optically active 3-substituted-3-formyl-2-hydroxypropanoic acid compound (4) after isolation but without purification, and mixing them; a method of adding the reaction mixture after completion of the aldol reaction which contains optically active 3-substituted-3-formyl-2-hydroxypropanoic acid compound (4), or optically active 3-substituted-3-formyl-2-hydroxypropanoic acid compound (4) after isolation but without purification, to $Ph_3P=CHCO_2R^9$, and mixing them; and the like. Among them, a method of adding $Ph_3P=CHCO_2R^9$ to the reaction mixture after completion of the aldol reaction which contains optically active 3-substituted-3-formyl-2-hydroxypropanoic acid compound (4), or optically active 3-substituted-3-formyl-2-hydroxypropanoic acid compound (4) after isolation but without purification, and mixing them is preferable in view of convenient operation.

The Wittig reaction is carried out preferably within the range of 0-100° C., more preferably within the range of 10-40° C., particularly preferably within the range of 20-30° C., though depending on the kind of $Ph_3P=CHCO_2R^9$.

While the reaction time varies depending on the kind of $Ph_3P=CHCO_2R^9$ and the reaction temperature, it is preferably 10 min-50 hr, more preferably 30 min-20 hr, particularly preferably 1-10 hr.

The progress of the reaction can be confirmed by an analysis means such as thin layer chromatography, gas chromatography, high performance liquid chromatography and the like.

Optically active α,β-unsaturated ester compound (6) contained in thus obtained reaction mixture can be isolated by subjecting the reaction mixture to a post-treatment using a conventional method (e.g., neutralization, extraction, washing with water, distillation, crystallization etc.), and purified by subjecting optically active α,β-unsaturated ester compound (6) to recrystallization treatment, extraction purification treatment, distillation treatment, adsorption treatment using activated carbon, silica, alumina and the like, or chromatography treatment using silica gel column chromatography and the like.

The diastereo ratio (syn/anti ratio) and enantiomeric excess of the obtained optically active acetal compound (5) or optically active α,β-unsaturated ester compound (6) are measured. The measured diastereo ratio (syn/anti ratio) and enantiomeric excess correspond to those of optically active 3-substituted-3-formyl-2-hydroxypropanoic acid compound (4).

When $R^2$ and $R^3$ in aldehyde (2) are different groups, in the aldol reaction step of the present invention, the anti-form of optically active 3-substituted-3-formyl-2-hydroxypropanoic acid compound (4) is preferentially obtained. The diastereoselectivity showing a diastereo ratio (syn/anti ratio) of, for example, 50/50 or more, or, for example, 20/80 or more, is available.

In the aldol reaction step of the present invention, when optically active pyrrolidine compound (3a) wherein the absolute configuration of C** is S-configuration, i.e., an optically active pyrrolidine compound represented by the formula (3a-S):

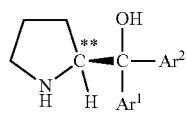

(3a-S)

wherein $Ar^1$ and $Ar^2$ are as defined above,
is used as a catalyst, optically active 3-substituted-3-formyl-2-hydroxypropanoic acid compound (4) wherein the absolute configuration of C* is R-configuration, i.e., an optically active 3-substituted-3-formyl-2-hydroxypropanoic acid compound represented by the formula (4R):

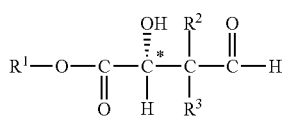

(4R)

wherein $R^1$, $R^2$ and $R^3$ are as defined above,
is preferentially obtained.

On the other hand, when optically active pyrrolidine compound (3a) wherein the absolute configuration of C** is R-configuration, i.e., an optically active pyrrolidine compound represented by the formula (3a-R):

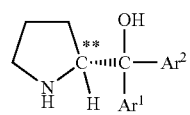

(3a-R)

wherein $Ar^1$ and $Ar^2$ are as defined above,
is used as a catalyst, optically active 3-substituted-3-formyl-2-hydroxypropanoic acid compound (4) wherein the absolute configuration of C* is S-configuration, i.e., an optically active 3-substituted-3-formyl-2-hydroxypropanoic acid compound represented by the formula (4S):

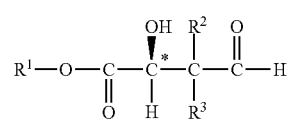

(4S)

wherein $R^1$, $R^2$ and $R^3$ are as defined above,
is preferentially obtained.

Therefore, in the aldol reaction step in the present invention, the enantioselectivity showing an enantiomeric excess of, for example, 50ee % or more, or, for example, 80ee % or more, is available.

EXAMPLES

The present invention is explained more specifically in the following by referring to Examples.

Ethyl glyoxylate (polymer) (in toluene, 47%; purchased from TCI (Tokyo Chemical Industry Co., Ltd.); catalog number: G0242) was used. All of liquid aldehyde and solvent other than ethyl glyoxylate were distilled prior to use.

All of the reaction was performed under an argon atmosphere, and monitored using thin layer chromatography using Merck 60 $F_{254}$ precoated silica gel plate (0.25 mm thickness). Preparative thin layer chromatography was performed using Wakogel B-5F purchased from Wako Pure Chemical Industries, Ltd. (Japan, Tokyo). Flash chromatography was performed using silica gel 60N manufactured by Kanto Chemical Co., Inc (Japan, Tokyo).

FT-IR spectrum was measured using JASCO FT/IR-410 spectrometer.

$^1H$ and $^{13}C$-NMR spectrum was measured using Bruker AM400 (400 MHz for $^1H$-NMR, 100 MHz for $^{13}C$-NMR) apparatus. $^1H$-NMR data was reported as chemical shift (δppm), multiplicity (s=singlet, d=doublet, t=triplet, q=quartet, m=multiplet), coupling constant (Hz), integral and assignment. $^{13}C$-NMR data was reported as a chemical shift.

High resolution mass spectrum analysis (HRMS) was performed using Bruker ESI-TOF MS and APCI-TOF MS.

HPLC analysis was performed using HITACHI Elite LaChrom Series HPLC using CHIRALCEL OB-H (0.46 cm×25 cm), CHIRALPAK IA (0.46 cm×25 cm) and CHIRALPAK IB (0.46 cm×25 cm), while monitoring using UV detection at respective suitable wavelengths.

Example 1-1 and 1-2

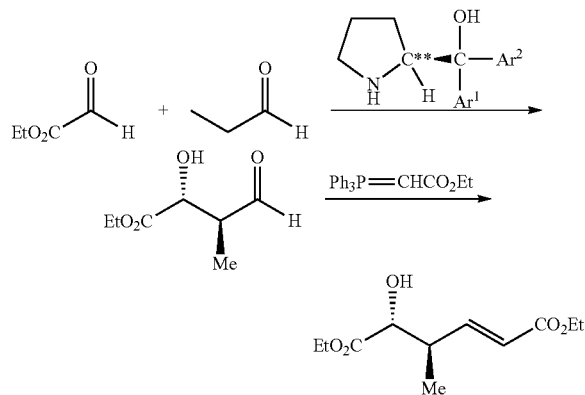

a: Ar¹, Ar² = phenyl
b: Ar¹, Ar² = 3,5-CF₃-phenyl

To ethyl glyoxylate polymer (108.6 mg, 47% toluene solution, 0.5 mmol) were added an optically active pyrrolidine compound (catalyst a or b, 0.05 mmol) as a catalyst, and propanal (145 mg, 2.5 mmol). The reaction mixture was stirred at 23° C. for 24 hr, and the toluene and excess of propanal were evaporated under reduced pressure. To the residue were added benzene (5 mL) and Ph₃P=CHCO₂Et (348 mg, 1.0 mmol). The reaction mixture was stirred at 23° C. for 24 hr, and filtered through silica gel pad to quench the Wittig reaction, and the filtrate was concentrated under reduced pressure. The residue was purified by preparative thin layer chromatography (ethyl acetate:hexane=1:2) to give 1,6-diethyl (4R,5R,E)-5-hydroxy-4-methylhex-2-enedioate. The yield, syn/anti ratio and enantiomeric excess are shown in Table 1. The yield is calculated as a yield in 2 steps. The syn/anti ratio was measured by ¹H-NMR spectrum. The enantiomeric excess was measured by HPLC using CHIRALCEL OB-H column (ⁱPrOH:hexane=1:100, 1 mL/min).

¹H-NMR (CDCl₃, 400 MHz): δ 1.17(3H,d,J=6.8 Hz), 1.20-1.31(6H,m), 2.73-2.84(1H,m), 4.11-4.30(5H,m), 5.81 (1H,dd,J=15.6,0.8 Hz), 6.85(1H,dd,J=15.6,0.8 Hz);

¹³C-NMR (CDCl₃, 100 MHz): δ 14.1, 15.6, 40.4, 60.3, 61.9, 73.7, 122.6, 147.5, 166.1, 173.4;

IR (neat): ν 3481, 2981, 1719, 1654, 1456, 1370, 1278, 1183, 1029, 865 cm⁻¹;

HRMS (ESI): [M+Na] [C₁₁H₁₈O₅Na]: Calculated 253.1046. Found 253.1058.

$[\alpha]_D^{18°\ C.}$ +8.7 (c=0.6, CHCl₃);

the retention time of the minor enantiomer=22.8 min, and the retention time of the major enantiomer=31.8 min.

Example 1-3-1-8

The steps were performed in the same manner as in Example 1-1 except that ethyl glyoxylate polymer was concentrated, and to the residue were added (S)-2-[bis(3,5-bis (trifluoromethyl)phenyl)hydroxymethyl]pyrrolidine (catalyst b, 26.3 mg, 0.05 mmol), propanal (145 mg, 2.5 mmol) and a solvent (0.5 ml) shown in Table 1. The yield, syn/anti ratio and enantiomeric excess are shown in Table 1.

Example 1-9

The steps were performed in the same manner as in Example 1-1 except that ethyl glyoxylate polymer was concentrated, and to the residue were added (S)-2-[bis(3,5-bis (trifluoromethyl)phenyl)hydroxymethyl]pyrrolidine (catalyst b, 26.3 mg, 0.05 mmol), propanal (145 mg, 2.5 mmol), acetonitrile (0.5 ml, 1 M) and water (27.3 μL, 1.5 mmol). The yield, syn/anti ratio and enantiomeric excess are shown in Table 1.

Example 1-10

The steps were performed in the same manner as in Example 1-1 except that ethyl glyoxylate polymer was concentrated, and to the residue were added (S)-2-[bis(3,5-bis (trifluoromethyl)phenyl)hydroxymethyl]pyrrolidine (catalyst b, 26.3 mg, 0.05 mmol), propanal (43.5 mg, 0.75 mmol), acetonitrile (0.5 ml, 1 M) and water (27.3 μL, 1.5 mmol). The yield, syn/anti ratio and enantiomeric excess are shown in Table 1.

TABLE 1

| Example | catalyst | solvent | yield (%) | syn:anti | ee % |
|---|---|---|---|---|---|
| 1-1 | a | toluene | 57 | 1:4.6 | 86 |
| 1-2 | b | toluene | 59 | 1:4.3 | 92 |
| 1-3 | b | MeOH | 18 | 1:4.9 | 90 |
| 1-4 | b | DMF | 41 | 1:2.0 | 62 |
| 1-5 | b | CHCl₃ | 55 | 1:3.8 | 94 |
| 1-6 | b | THF | 50 | 1:3.7 | 95 |
| 1-7 | b | H₂O | 67 | 1:3.6 | 92 |
| 1-8 | b | CH₃CN | 73 | 1:4.4 | 98 |
| 1-9 | b | aq•CH₃CN | 86 | 1:4.1 | 96 |
| 1-10 | b | aq•CH₃CN | 93 | 1:9.8 | 98 |

Example 2-1-2-4

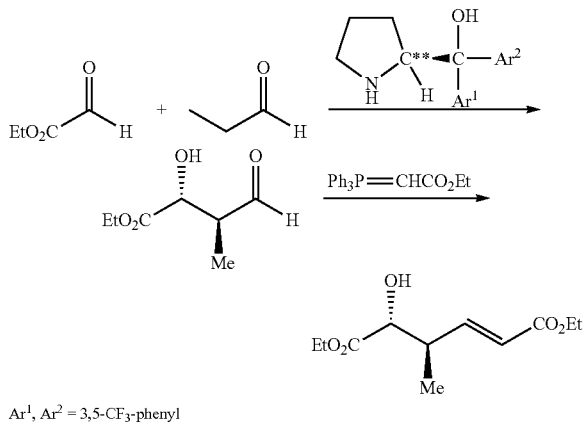

Ar¹, Ar² = 3,5-CF₃-phenyl

To ethyl glyoxylate polymer obtained by concentrating 47% toluene solution (108.6 mg, 0.5 mmol) were added (S)-2-[bis(3,5-bis(trifluoromethyl)phenyl)hydroxymethyl]pyrrolidine in an amount shown in Table 2 (the amount relative to ethyl glyoxylate (in monomer amount)), propanal (43.5 mg, 0.75 mmol), acetonitrile (0.5 ml, 1 M) and water (27.3 μL, 1.5 mmol). The reaction mixture was stirred at 23° C. for 24 hr, and Ph₃P=CHCO₂Et (348 mg, 1.0 mmol) was added thereto.

The reaction mixture was stirred at 23° C. for 24 hr, and filtered through silica gel pad to quench the Wittig reaction, and the filtrate was concentrated under reduced pressure. The residue was purified by preparative thin layer chromatography (ethyl acetate:hexane=1:2) to give 1,6-diethyl (4R,5R,E)-5-hydroxy-4-methylhex-2-enedioate. The yield, syn/anti ratio and enantiomeric excess are shown in Table 2. The yield is calculated as a yield in 2 steps. The syn/anti ratio was measured by $^1$H-NMR spectrum. The enantiomeric excess was measured by HPLC using CHIRALCEL OB-H column ($^i$PrOH:hexane=1:100, 1 mL/min).

TABLE 2

| Example | catalyst (mol %) | time (h) | yield (%) | syn:anti | ee (%) |
|---------|------------------|----------|-----------|----------|--------|
| 2-1 | 10 | 20 | 93 | 1:9.8 | 98 |
| 2-2 | 5 | 30 | quant. | 1:7.6 | 98 |
| 2-3 | 2 | 40 | quant. | 1:7.3 | 99 |
| 2-4 | 1 | 48 | 61 | 1:11.5 | 99 |

Example 3-1-3-6

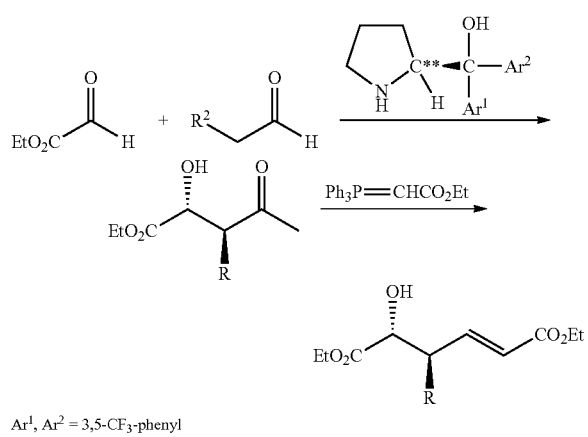

Ar$^1$, Ar$^2$ = 3,5-CF$_3$-phenyl

To ethyl glyoxylate polymer obtained by concentrating 47% toluene solution (108.6 mg, 0.5 mmol) were added (S)-2-[bis(3,5-bis(trifluoromethyl)phenyl)hydroxymethyl]pyrrolidine (26.3 mg, 0.05 mmol), acetonitrile (0.5 mL, 1.0 M), water (27.3 μL, 1.5 mmol) and the corresponding aldehyde (0.75 mmol). The reaction mixture was stirred at 23° C. for 24 hr, and Ph$_3$P=CHCO$_2$Et (348 mg, 1.0 mmol) was added thereto. The reaction mixture was stirred at 23° C. for 24 hr, and filtered through silica gel pad to quench the Wittig reaction, and the filtrate was concentrated under reduced pressure. The residue was purified by preparative thin layer chromatography (ethyl acetate:hexane=1:2) to give the corresponding α,β-unsaturated ester. The yield, syn/anti ratio and enantiomeric excess are shown in Table 3. The yield is calculated as a yield in 2 steps. The syn/anti ratio was measured by $^1$H-NMR spectrum.

1-tert-butyl 6-ethyl (R,E)-5-hydroxy-hex-2-enedioate

Example 3-1

$^1$H-NMR (CDCl$_3$, 400 MHz): δ 1.27(3H,t,J=7.2 Hz), 1.29 (9H,s), 2.46-2.56(1H,m), 2.60-2.70(1H,m), 3.02(1H,br-s), 4.18-4.30(3H,m), 5.82(1H,d,J=15.6 Hz), 6.79(1H,dt,J=15.6, 7.2 Hz);

$^{13}$C-NMR (CDCl$_3$, 100 MHz): δ 14.1, 28.0, 36.8, 61.9, 69.3, 80.3, 126.3, 141.3, 165.3, 173.9;

IR (neat): ν 3481, 2980, 2936, 1715, 1655, 1369, 1153, 1106, 1027, 981, 850 cm$^{-1}$;

HRMS (ESI): [M+Na] [C$_{12}$H$_{20}$O$_5$Na]: Calculated 267.1203. Found 267.1204.

[α]$_D^{17°\,C.}$ +10.0 (c=1.9, CHCl$_3$);

The enantiomeric excess was measured by HPLC using CHIRALCEL OB-H column ($^i$PrOH:hexane=1:10, 1 mL/min) (the retention time of the minor enantiomer=9.9 min, and the retention time of the major enantiomer=13.8 min).

1,6-diethyl (4R,5R,E)-5-hydroxy-4-methylhex-2-enedioate

Example 3-2

$^1$H-NMR (CDCl$_3$, 400 MHz): δ 1.17(3H,d,J=6.8 Hz), 1.20-1.31(6H,m), 2.73-2.84(1H,m), 4.11-4.30(5H,m), 5.81 (1H,dd,J=15.6,0.8 Hz), 6.85(1H,dd,J=15.6,0.8 Hz);

$^{13}$C-NMR (CDCl$_3$, 100 MHz): δ 14.1, 15.6, 40.4, 60.3, 61.9, 73.7, 122.6, 147.5, 166.1, 173.4;

IR (neat): ν 3481, 2981, 1719, 1654, 1456, 1370, 1278, 1183, 1029, 865 cm$^{-1}$;

HRMS (ESI): [M+Na] [C$_{11}$H$_{18}$O$_5$Na]: Calculated 253.1046. Found 253.1058.

[α]$_D^{18°\,C.}$ +8.7 (0.6, CHCl$_3$);

The enantiomeric excess was measured by HPLC using CHIRALCEL OB-H column ($^i$PrOH:hexane=1:100, 1 mL/min) (the retention time of the minor enantiomer=22.8 min, and the retention time of the major enantiomer=31.8 min).

1-tert-butyl 6-ethyl (4R,5R,E)-5-hydroxy-4-ethyl-hex-2-enedioate

Example 3-3

$^1$H-NMR (CDCl$_3$, 400 MHz): δ 0.92(3H,t,J=7.6 Hz), 1.28 (3H,t,J=6.8 Hz), 1.45(9H,s), 1.50-1.75(4H,m), 2.47(1H,tq, J=2.8,9.2 Hz), 2.80(1H,br-s), 4.16-4.32(3H,m), 5.72(1H,dd, J=0.8,15.6 Hz), 6.66(1H,dd,J=9.2,15.6 Hz);

$^{13}$C-NMR (CDCl$_3$, 100 MHz): δ 11.7, 14.1, 23.4, 28.0, 47.7, 61.7, 72.3, 80.1, 125.5, 145.0, 165.2, 173.7;

IR (neat): ν 3488, 2979, 2935, 1729, 1724, 1654, 1368, 1157, 1026, 982 cm$^{-1}$;

HRMS (ESI): [M+Na] [C$_{14}$H$_{24}$O$_5$Na]: Calculated 295.1516. Found: 95.1519.

[α]$_D^{18°\,C.}$ −14.8 (c=1.1, CHCl$_3$);

The enantiomeric excess was measured by HPLC using CHIRALPAK IA column ($^i$PrOH:hexane=1:30, 1 mL/min) (the retention time of the minor enantiomer=15.1 min, and the retention time of the major enantiomer=12.3 min).

1-tert-butyl 6-ethyl (4R,5R,E)-5-hydroxy-4-normal-propylhex-2-enedioate

Example 3-4

$^1$H-NMR (CDCl$_3$, 400 MHz): δ 0.91(3H,t,J=7.2 Hz), 1.29 (3H,t,J=6.8 Hz), 1.29-1.38(1H,m), 1.46(9H,s), 1.48-1.66 (4H,m), 2.59(1H,ddt,J=2.8,5.6,8.8 Hz), 4.18-4.32(3H,m), 5.72(1H,d,J=16.0 Hz), 6.67(1H,dd,J=9.6,16.0 Hz);

$^{13}$C-NMR (CDCl$_3$, 100 MHz): δ 13.9, 14.2, 20.3, 28.1, 32.6, 45.8, 61.9, 72.7, 80.3, 125.5, 145.2, 165.3, 173.8;

R(neat): ν 3470, 2961, 2931, 1733, 1716, 1454, 1368, 1250, 1158, 1139 cm$^{-1}$;

HRMS (ESI): [M+Na] [C$_{15}$H$_{26}$O$_5$Na]: Calculated 309.1672. Found: 306.1678.

[α]$_D^{19°\ C.}$ −14.6 (c=2.2, CHCl$_3$);

The enantiomeric excess was measured by HPLC using CHIRALPAK IA column ($^i$PrOH:hexane=1:100, 1 mL/min) after 2,4-dinitrobenzoylation of the Wittig resultant product (the retention time of the minor enantiomer=50.6 min, and the retention time of the major enantiomer=31.0 min).

1-tert-butyl 6-ethyl (4R,5R,E)-5-hydroxy-4-iso-propylhex-2-enedioate

Example 3-5

$^1$H-NMR (CDCl$_3$, 400 MHz): δ 0.90(3H,d,J=6.8 Hz), 1.06 (3H,d,J=6.4 Hz), 1.28(3H,t,J=7.2 Hz), 1.46(9H,s), 1.97(1H, dq,J=9.2,6.8 Hz), 2.20(1H,dt,J=2.4,9.6 Hz), 2.78(1H,br-s), 4.20(1H,dq,J=7.2,10.4 Hz), 4.27(1H,dq,J=7.2,10.4 Hz), 4.40 (1H,br-s), 5.69(1H,d,J=15.6 Hz), 6.70(1H,dd,J=10.4,15.6 Hz);

$^{13}$C-NMR (CDCl$_3$, 100 MHz): δ 14.0, 20.2, 20.9, 27.9, 28.0, 52.8, 61.7, 70.8, 80.1, 125.9, 144.4, 164.9, 174.0;

IR (neat): ν 3442, 2974, 2931, 1733, 1716, 1366, 1282, 1246, 1157, 1143 cm$^{-1}$;

HRMS (ESI): [M+Na] [C$_{15}$H$_{26}$C$_5$Na]: Calculated 309.1672. Found 309.1683.

[α]$_D^{20°\ C.}$ −27.4 (c=0.87, CHCl$_3$);

The enantiomeric excess was measured by HPLC using CHIRALPAK IA column ($^i$PrOH:hexane=1:100, 1 mL/min) after 2,4-dinitrobenzoylation of the Wittig resultant product (the retention time of the minor enantiomer=33.9 min, and the retention time of the major enantiomer=26.3 min).

1-tert-butyl 6-ethyl (4S,5R,E)-5-hydroxy-4-benzyl-hex-2-enedioate

Example 3-6

$^1$H-NMR (CDCl$_3$, 400 MHz): δ 1.25(3H,t,J=7.2 Hz), 1.45 (9H,s), 2.76-2.90 (2H, m), 2.96 (1H, dd, J=8.4, 12.4 Hz), 4.09 (1H, dd, J=2.0, 4.4 Hz), 4.16(1H,dq,J=7.2,10.8 Hz), 4.25(1H, dq,J=7.2,10.8 Hz), 5.72(1H,d,J=15.6 Hz), 6.76(1H,dq,J=6.8, 15.6 Hz), 7.32-7.22(5H,m);

$^{13}$C-NMR (CDCl$_3$, 100 MHz): δ 14.2, 28.1, 36.8, 47.4, 61.9, 70.8, 80.3, 125.7, 126.4, 128.5, 129.3, 138.6, 144.2, 165.1, 173.9;

IR (neat): ν 3500, 2979, 1714, 1652, 1456, 1368, 1319, 1253, 1149, 1110, 985 cm$^{-1}$;

HRMS (ESI): [M+Na] [C$_{19}$H$_{26}$O$_5$Na]: Calculated 356.1672. Found 357.1668.

[α]$_D^{20°\ C.}$ −47.2 (c=0.63, CHCl$_3$);

The enantiomeric excess was measured by HPLC using CHIRALPAK IB column ($^i$PrOH:hexane=1:100, 1 mL/min) after benzoylation of the Wittig resultant product (the retention time of the minor enantiomer=17.9 min, and the retention time of the major enantiomer=15.6 min).

Example 3-7-3-8

In the same manner as in Example 3-1 except that to ethyl glyoxylate polymer obtained by concentrating 47% toluene solution (162.9 mg, 0.75 mmol) were added (S)-2-[bis(3,5-bis(trifluoromethyl)phenyl)hydroxymethyl]pyrrolidine (26.3 mg, 0.05 mmol), acetonitrile (0.25 mL, 0.5 M), water (27.3 μL, 1.5 mmol) and the corresponding aldehyde (0.5 mmol), the reaction mixture was stirred at 5° C. for 38 hr, and Ph$_3$P=CHCO$_2$Et (348 mg, 1.0 mmol) was added thereto, the corresponding α,β-unsaturated ester was obtained. The yield, syn/anti ratio and enantiomeric excess are shown in Table 3, in which the yield in 2 steps is calculated. The syn/anti ratio was measured by $^1$H-NMR spectrum.

1,6-diethyl (4S,5R,E)-5-hydroxy-4-(p-methoxybenzoylmethyl)hex-2-enedioate

Example 3-8

$^1$H-NMR (CDCl$_3$, 400 MHz): δ 1.27(3H,dt,J=3.2,7.2 Hz), 2.95-3.03(2H,m), 3.55(1H,dd,J=5.6,9.2 Hz), 3.68(1H,t,J=8.8 Hz), 3.81(3H,s), 4.17(2H,q,J=7.2 Hz), 4.18-4.26(2H,m), 4.43-4.52(2H,m), 5.87(1H,dd,J=0.8,15.6 Hz), 6.80(1H,dd, J=9.2,15.6 Hz), 6.88(2H,br-d,J=8.8 Hz), 7.25(2H,br-d,J=8.8 Hz);

$^{13}$C-NMR (CDCl$_3$, 100 MHz): δ 14.2, 46.0, 55.3, 60.4, 62.0, 68.9, 70.1, 73.1, 113.8, 124.9, 129.4, 129.9, 142.8, 159.3, 165.8, 173.7;

IR (neat): ν 3533, 2983, 2837, 1740, 1724, 1613, 1514, 1466, 1368, 1177, 1033, 820 cm$^{-1}$;

HRMS (ESI): [M+Na] [C$_{19}$H$_{26}$C$_7$Na]: Calculated 389.1571. Found 389.1580.

[α]$_D^{19°\ C.}$ −5.3 (c=0.70, CHCl$_3$);

The enantiomeric excess was measured by HPLC using CHIRALPAK IC column ($^i$PrOH:hexane=1:10, 1 mL/min) after benzoylation of the Wittig resultant product (the retention time of the minor enantiomer=17.6 min, and the retention time of the major enantiomer=23.8 min).

Example 3-9-3-11

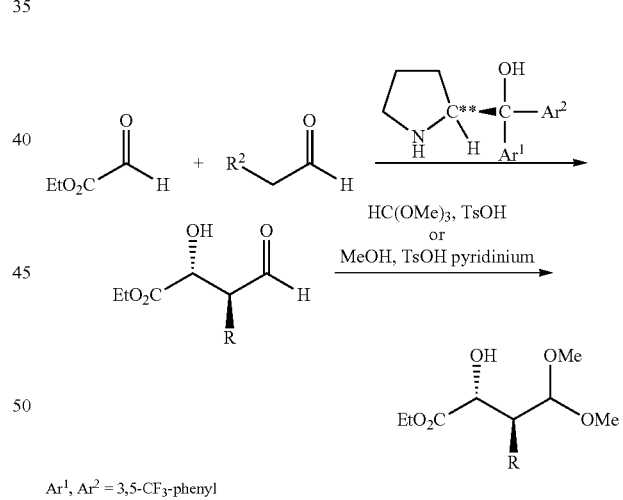

Ar$^1$, Ar$^2$ = 3,5-CF$_3$-phenyl

The reaction was carried out by the following Method A or Method B.

Method A

To ethyl glyoxylate polymer obtained by concentrating 47% toluene solution (108.6 mg, 0.5 mmol) were added (S)-2-[bis(3,5-bis(trifluoromethyl)phenyl)hydroxymethyl]pyrrolidine (26.3 mg, 0.05 mmol), acetonitrile (0.5 mL, 1.0 M), water (27.3 μL, 1.5 mmol) and the corresponding aldehyde (0.75 mmol). The reaction mixture was stirred at 23° C. for 48 hr, and the solvent and excess aldehyde were evaporated under reduced pressure. To the residue were added methanol (1.0 ml, 24.7 mmol) and pyridinium p-toluenesulfonate (12.6 mg, 0.05 mmol), and the reaction mixture was stirred at 50° C. for 5 hr, and quenched with saturated aqueous sodium hydrogen carbonate solution. The organic substance was extracted with chloroform three times, and the extract was dried over anhydrous $Na_2SO_4$, and filtered, and the filtrate was concentrated under reduced pressure. The residue was purified by column chromatography (ethyl acetate:hexane=1:10) to give an acetal resultant product. The yield, syn/anti ratio and enantiomeric excess are shown in Table 3, in which the yield in 2 steps is calculated. The syn/anti ratio was measured by $^1$H-NMR spectrum. The enantiomeric excess was measured by HPLC with chiral column after conversion to the corresponding 2,4-dinitrobenzoate.

Method B

To ethyl glyoxylate polymer obtained by concentrating 47% toluene solution (108.6 mg, 0.5 mmol) were added (S)-2-[bis(3,5-bis(trifluoromethyl)phenyl)hydroxymethyl]pyrrolidine (26.3 mg, 0.05 mmol), acetonitrile (0.5 mL, 1.0 M), water (27.3 μL, 1.5 mmol) and the corresponding aldehyde (0.75 mmol). The reaction mixture was stirred at 23° C. for 48 hr, and trimethyl orthoformate (274 μL, 2.5 mmol) and p-toluenesulfonic acid monohydrate (9.5 mg, 0.05 mmol) were added thereto. The reaction was quenched with saturated aqueous sodium hydrogen carbonate solution. The organic substance was extracted with chloroform three times, and the extract was dried over anhydrous $Na_2SO_4$, and filtered, and the filtrate was concentrated under reduced pressure. The residue was purified by column chromatography (ethyl acetate:hexane=1:10) to give an acetal resultant product. The yield, syn/anti ratio and enantiomeric excess are shown in Table 3, in which the yield in 2 steps is calculated. The syn/anti ratio was measured by $^1$H-NMR spectrum. The enantiomeric excess was measured by HPLC with chiral column after conversion to the corresponding 2,4-dinitrobenzoate.

ethyl (2R,3S)-2-hydroxy-4,4-dimethoxy-3-methylbutanoate

Example 3-9

$^1$H-NMR (CDCl$_3$, 400 MHz): δ 1.05(3H,d,J=7.6 Hz), 1.28 (3H,t,J=7.2 Hz), 3.12(1H,s), 2.32(1H,d of quint.,J=3.2,7.2 Hz), 3.31(3H,s), 3.32(3H,s), 4.21(1H,q,J=7.2 Hz), 4.30(1H, d,J=7.6 Hz);

$^{13}$C-NMR (CDCl$_3$, 100 MHz): δ 12.7, 14.1, 39.7, 53.0, 55.7, 61.4, 72.7, 106.0, 174.4;

IR (neat): ν 3501, 2982, 2939, 1733, 1464, 1256, 1226, 1131, 1059, 955 cm$^{-1}$;

HRMS (ESI): [M+Na] [C$_9$H$_{18}$O$_5$Na]: Calculated 229.1046. Found 229.1054.

$[\alpha]_D^{17° C.}$ −17.0 (c=1.0, CHCl$_3$);

The enantiomeric excess was measured by HPLC using CHIRALPAK IA column ($^i$PrOH:hexane=1:50, 1 mL/min) (the retention time of the minor enantiomer=22.9 min, and the retention time of the major enantiomer=20.3 min).

ethyl (2R,3S)-3-benzyloxy-4,4-dimethoxy-2-hydroxybutanoate

Example 3-10

$^1$H-NMR (CDCl$_3$, 400 MHz): δ 1.28(3H,t,J=6.8 Hz), 3.08 (1H,d,J=5.2 Hz), 3.40(3H,s), 3.45(3H,s), 3.80(1H,dd,J=2.4, 7.2 Hz), 4.23(2H,q,J=7.2 Hz), 4.41(1H,dd,J=2.4,4.8 Hz), 4.54(1H,d,J=7.2 Hz), 4.71(1H,d,J=12.0 Hz), 4.77(1H,d, J=12.0 Hz), 7.26-7.40(5H, m);

$^{13}$C-NMR (CDCl$_3$, 100 MHz): δ 14.1, 55.6, 56.1, 61.7, 71.2, 73.6, 80.8, 105.0, 127.7, 127.9, 128.4, 138.1, 172.2;

IR (neat): ν 3522, 3438, 2986, 2834, 1742, 1455, 1200, 1138, 1069, 1027, 745, 699 cm$^{-1}$;

HRMS (ESI): [M+Na] [C$_{15}$H$_{22}$C$_6$Na]: Calculated 321.1309. Found 321.1309.

$[\alpha]_D^{20° C.}$ −31.5 (c=0.90, CHCl$_3$);

The enantiomeric excess was measured by HPLC using CHIRALPAK IB column ($^i$PrOH:hexane=1:20, 1 mL/min) (the retention time of the minor enantiomer=20.7 min, and the retention time of the major enantiomer=26.2 min).

ethyl 3-phthalimidyl-4,4-dimethoxy-2-hydroxybutanoate

Example 3-11

Minor Diastereomer $^1$H-NMR (CDCl$_3$, 400 MHz): δ 1.17(3H,t,J=7.2 Hz), 3.26 (3H,s), 3.55(3H,s), 4.07(1H,dq,J=10.8,7.2 Hz), 4.20(1H,br-d,J=10.8 Hz), 4.68-4.77(2H,m), 5.24(1H,d,J=8.4 Hz), 7.74 (2H,dd,J=3.2,5.6 Hz), 7.85(2H,dd,J=3.2,5.6 Hz);

$^{13}$C-NMR (CDCl$_3$, 100 MHz): δ 14.0, 53.0, 54.8, 55.9, 61.6, 70.9, 99.6, 123.7, 131.5, 134.4, 168.7, 172.1;

IR (neat): ν 3472, 2941, 1775, 1747, 1715, 1389, 1207, 1123, 1069, 772 cm$^{-1}$;

HRMS (ESI): [M+Na] [C$_{16}$H$_{19}$NO$_7$Na]: Calculated 360.1054. Found: 360.1063.

$[\alpha]_D^{21° C.}$ +25.8 (c=1.34, CHCl$_3$);

The enantiomeric excess was measured by HPLC using CHIRALPAK IB column ($^i$PrOH:hexane=1:30, 1 mL/min) (the retention time of the minor enantiomer=21.9 min, and the retention time of the major enantiomer=19.4 min).

ethyl 3-phthalimidyl-4,4-dimethoxy-2-hydroxybutanoate

Example 3-11

Major Diastereomer $^1$H-NMR (CDCl$_3$, 400 MHz): δ 1.32(3H,t,J=7.2 Hz), 3.27 (3H,s), 3.49(3H,s), 3.67(1H,br-d,J=3.6 Hz), 4.29(2H,dq, J=2.4,7.2 Hz), 4.55(1H,br-t,J=3.6 Hz), 4.81(1H,dd,J=3.6,8.8 Hz), 5.42(1H,d,J=8.8 Hz), 7.73(2H,dd,J=3.2,5.2 Hz), 7.85 (2H,dd,J=3.2,5.2 Hz);

$^{13}$C-NMR (CDCl$_3$, 100 MHz): δ 14.0, 52.8, 54.7, 56.0, 62.1, 70.6, 99.7, 123.5, 131.7, 134.2, 168.2, 171.6;

IR (neat): ν 3478, 2941, 2838, 1776, 1716, 1469, 1388, 1216, 1109, 1071, 722 cm$^{-1}$;

HRMS (ESI): [M+Na] [C$_{16}$H$_{19}$NO$_7$Na]: Calculated 360.1054. Found 360.106.

$[\alpha]_D^{21° C.}$ −33.5 (c=0.52, CHCl$_3$);

The enantiomeric excess was measured by HPLC using CHIRALPAK IB column ($^i$PrOH:hexane=1:30, 1 mL/min) (the retention time of the minor enantiomer=35.3 min, and the retention time of the major enantiomer=30.7 min).

TABLE 3

| Example | resultant product | yield (%) | syn:anti | ee (%) |
|---|---|---|---|---|
| 3-1 | EtO$_2$C–CH(OH)–CH$_2$–CH=CH–CO$_2$t-Bu | 74 | — | 90 |
| 3-2 | EtO$_2$C–CH(OH)–CH(Me)–CH=CH–CO$_2$Et | 93 | 1:9.8 | 98 |
| 3-3 | EtO$_2$C–CH(OH)–CH(Et)–CH=CH–CO$_2$t-Bu | quant. | 1:16 | 92 |
| 3-4 | EtO$_2$C–CH(OH)–CH(n-Pr)–CH=CH–CO$_2$t-Bu | 89 | 1:19 | 96 |
| 3-5 | EtO$_2$C–CH(OH)–CH(i-Pr)–CH=CH–CO$_2$t-Bu | quant. | 1:19 | 97 |
| 3-6 | EtO$_2$C–CH(OH)–CH(Bn)–CH=CH–CO$_2$t-Bu | 92 | 1:>20 | >99 |
| 3-7 | EtO$_2$C–CH(OH)–CH(Bn)–CH=CH–CO$_2$Et | 78 | 1:>20 | 97 |
| 3-8 | EtO$_2$C–CH(OH)–CH(CH$_2$OPMB)–CH=CH–CO$_2$Et | 95 | 1:6.8 | 99 |
| 3-9 | EtO$_2$C–CH(OH)–CH(Me)–CH(OMe)–OMe | 74 | 1:9.7 | 99 |
| 3-10 | EtO$_2$C–CH(OH)–CH(OBn)–CH(OMe)–OMe | 78 | 1:>20 | 98 |
| 3-11 | EtO$_2$C–CH(OH)–CH(NPhth)–CH(OMe)–OMe | 88 | 1:1.4 | 91, 91 |

INDUSTRIAL APPLICABILITY

According to the production method of the present invention, since the reactivity of the reaction in the presence of optically active pyrrolidine compound (3) as a catalyst is superior even when glyoxylic acid compound (1-1) or (1-2) is used in the form of a polymer, a commercially available product can be used, and a complicated step such as thermal decomposition and distillation immediately before use is not necessary. In addition, reaction under aqueous conditions is also possible. Furthermore, when reacted in toluene, a commercially available product can be advantageously used directly without evaporating toluene.

Using optically active pyrrolidine compound (3) having a particular structure and a particular solvent, an optically active 3-substituted-3-formyl-2-hydroxypropanoic acid compound (4) can be produced in a high yield with superior enantioselectivity and diastereoselectivity (when R$^2$ and R$^3$ in aldehyde (2) are different groups).

The invention claimed is:

1. A method of producing an optically active 3-substituted-3-formyl-2-hydroxypropanoic acid compound of formula (4):

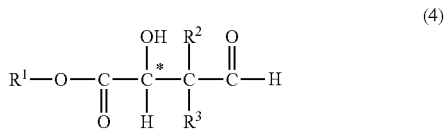

wherein

R$^1$ is (i) a C$_1$-C$_{20}$ hydrocarbon group optionally having substituent(s) selected from the following Group G1 or (ii) a hydrogen atom, R$^2$ and R$^3$ are each independently (i) a C$_1$-C$_{20}$ hydrocarbon group optionally having substituent(s) selected from the following Group G1, (ii) a C$_1$-C$_{12}$ alkoxy group optionally having substituent(s) selected from the following Group G1, (iii) a heterocyclic group optionally having substituent(s) selected from the following Group G1 or (iv) a hydrogen atom, and the carbon atom marked with * is an asymmetric carbon atom, which comprises a step of reacting a glyoxylic acid compound of formula (1-1):

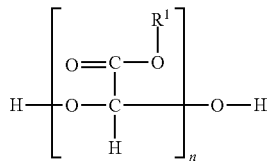

(1-1)

wherein R¹ is as defined above, and n is an integer of 2 or more, or a glyoxylic acid compound of formula (1-2):

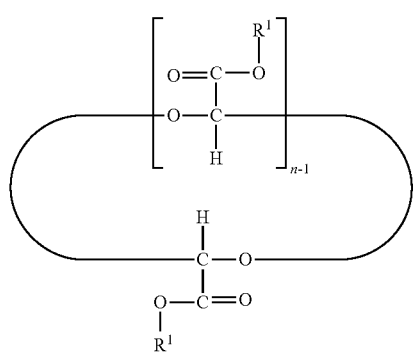

(1-2)

wherein R¹ and n are as defined above,
with an aldehyde of formula (2):

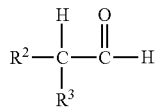

(2)

wherein R² and R³ are as defined above, in the presence of an optically active pyrrolidine compound of formula (3):

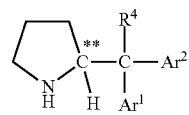

(3)

wherein
Ar¹ and Ar² are each independently (i) a phenyl group optionally having substituent(s) selected from the following Group G2, (ii) a $C_1$-$C_{12}$ chain hydrocarbon group, (iii) a $C_3$-$C_{12}$ alicyclic hydrocarbon group or (iv) a hydrogen atom,
R⁴ is (i) a hydrogen atom, (ii) a fluorine atom, (iii) a hydroxyl group, (iv) a $C_1$-$C_{12}$ alkoxy group, (v) a $C_1$-$C_{12}$ fluorinated alkyloxy group or (vi) a silyloxy group reprsented by —OSiR⁵R⁶R⁷,
wherein R⁵, R⁶ and R⁷ are each independently (i) a $C_1$-$C_8$ alkyl group or (ii) a $C_6$-$C_{20}$ aryl group, and
the carbon atom marked with ** is an asymmetric carbon atom;
Group G1 is (i) a $C_6$-$C_{20}$ aryl group optionally having substituent(s) selected from Group G2, (ii) an aromatic heterocyclic group optionally having substituent(s) selected from Group G2, (iii) a $C_1$-$C_{12}$ alkoxy group, (iv) a $C_1$-$C_{12}$ alkoxy group having $C_6$-$C_{20}$ aryl group(s) optionally having substituent(s) selected from Group G2, (v) a halogen atom, or (vi) an oxo group;
Group G2 is (i) a $C_1$-$C_{12}$ alkyl group, (ii) a $C_1$-$C_{12}$ alkoxy group, (iii) a $C_2$-$C_{13}$ alkoxycarbonyl group, (iv) a $C_1$-$C_{12}$ fluorinated alkyl group, (v) a $C_2$-$C_{13}$ acyl group, (vi) a nitro group, (vii) a cyano group, (viii) a protected amino group, or (ix) a halogen atom.

2. The method of claim 1, wherein the reaction is carried out in the presence of a solvent.

3. The method of claim 2, wherein the solvent is at least one selected from the group consisting of an aromatic hydrocarbon solvent, an alcohol solvent, a halogenated hydrocarbon solvent, an ether solvent, a nitrile solvent and water.

4. The method of claim 1, wherein the reaction is carried out within the range of 0-50° C.

5. The method of claim 1, wherein R³ is a hydrogen atom.

6. The method of claim 1, wherein R⁴ is a hydroxyl group, and Ar¹ and Ar² are each independently a phenyl group optionally having $C_1$-$C_{12}$ fluorinated alkyl group(s).

7. The method of claim 1, wherein R⁴ is a hydroxyl group, and Ar¹ and Ar² are both 3,5-bis(trifluoromethyl)phenyl groups.

8. The method of claim 6, wherein the absolute configuration of C** is S-configuration, and the absolute configuration of C* is R-configuration.

9. A method of producing an optically active acetal compound of formula (5):

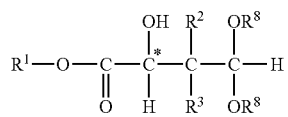

(5)

wherein
R¹, R² and R³ are as defined in claim 1,
R⁸ is a $C_1$-$C_8$ alkyl group, and
the carbon atom marked with * is an asymmetric carbon atom,
which comprises a step of reacting an optically active 3-substituted-3-formyl-2-hydroxypropanoic acid compound of formula (4), which is obtained according to the method of claim 1, with R⁸OH or HC(OR⁸)₃ wherein R⁸ is as defined above, in the presence of an acid catalyst.

10. A method of producing an optically active α,β-unsaturated ester compound of formula (6):

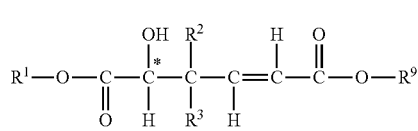

(6)

wherein
R¹, R² and R³ are as defined in claim 1,
R⁹ is a $C_1$-$C_8$ alkyl group, and
the carbon atom marked with * is an asymmetric carbon atom, which comprises a step of reacting an optically active 3-substituted-3-formyl-2-hydroxypropanoic acid compound of formula (4), which is obtained according to the method of claim 1, with Ph₃P=CHCO₂R⁹ wherein Ph is a phenyl group, and R⁹ is as defined above.

11. The method of claim 7, wherein the absolute configuration of C** is S-configuration, and the absolute configuration of C* is R-configuration.

\* \* \* \* \*